(12) United States Patent
Bremer et al.

(10) Patent No.: US 7,325,453 B2
(45) Date of Patent: Feb. 5, 2008

(54) ACTIVITY MONITORING

(75) Inventors: Joannes Gregorius Bremer, Eindhoven (NL); Paraskevas Dunias, Eindhoven (NL); Gillian Antoinette Mimnagh-Kelleher, Eindhoven (NL); Adrianus Petrus Johanna Maria Rommers, Eindhoven (NL); Wilhelmus Lambertus Marinus Cornelius Verhoeven, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/537,888

(22) PCT Filed: Nov. 21, 2003

(86) PCT No.: PCT/IB03/05323

§ 371 (c)(1),
(2), (4) Date: Jun. 7, 2005

(87) PCT Pub. No.: WO2004/052200

PCT Pub. Date: Jun. 24, 2004

(65) Prior Publication Data

US 2006/0123905 A1  Jun. 15, 2006

(30) Foreign Application Priority Data

Dec. 10, 2002 (EP) .................................. 02080216

(51) Int. Cl.
*G01P 3/04* (2006.01)

(52) U.S. Cl. .................. 73/510; 73/865.1; 73/865.3; 73/865.4; 340/669

(58) Field of Classification Search .................. 73/510, 73/514.34, 865.1, 865.3; 235/116; 340/573.1, 340/669
See application file for complete search history.

(56) References Cited

U.S. PATENT DOCUMENTS

| 5,181,181 | A | * | 1/1993 | Glynn ........................ 702/141 |
| 5,272,476 | A | * | 12/1993 | McArthur et al. ..... 340/870.13 |
| 5,317,304 | A | * | 5/1994 | Choi .......................... 340/571 |
| 5,573,013 | A | * | 11/1996 | Conlan ....................... 600/595 |
| 5,723,786 | A | * | 3/1998 | Klapman ................. 73/379.04 |
| 5,807,283 | A | * | 9/1998 | Ng ............................ 600/595 |
| 6,077,236 | A |   | 6/2000 | Cunningham |
| 6,122,960 | A | * | 9/2000 | Hutchings et al. ............ 73/493 |
| 6,201,476 | B1 | * | 3/2001 | Depeursinge et al. .... 340/573.1 |
| 6,466,821 | B1 | * | 10/2002 | Pianca et al. ................. 607/18 |
| 2002/0109600 | A1 | * | 8/2002 | Mault et al. ............. 340/573.1 |
| 2003/0014660 | A1 | * | 1/2003 | Verplaetse et al. .......... 713/200 |

FOREIGN PATENT DOCUMENTS

EP 0727242 A1 8/1996

OTHER PUBLICATIONS

"A continuous patient activity monitor: validation and relation to disability", D J Walker, P S Heslop C J Plummer, T Essex and S Chandler, IOP Publishing Ltd, Musuloskeletal Department, Freeman Hospital.*
Walker, Heslop, Plummer, Essex and Chandler, "A Continuous Patient Activity Monitor: Validation and Relation to Disability", Physiological Measurement, 18 (1997), Sep. 5, 1996, pp. 49-59.*

(Continued)

*Primary Examiner*—Hezron Williams
*Assistant Examiner*—Samir M. Shah

(57) ABSTRACT

An activity monitor is provided that can be cheaper and require lower power than existing activity monitors. A single output channel from a plurality of motion sensors is provided and monitored intermittently.

15 Claims, 3 Drawing Sheets

OTHER PUBLICATIONS

Figure 1:
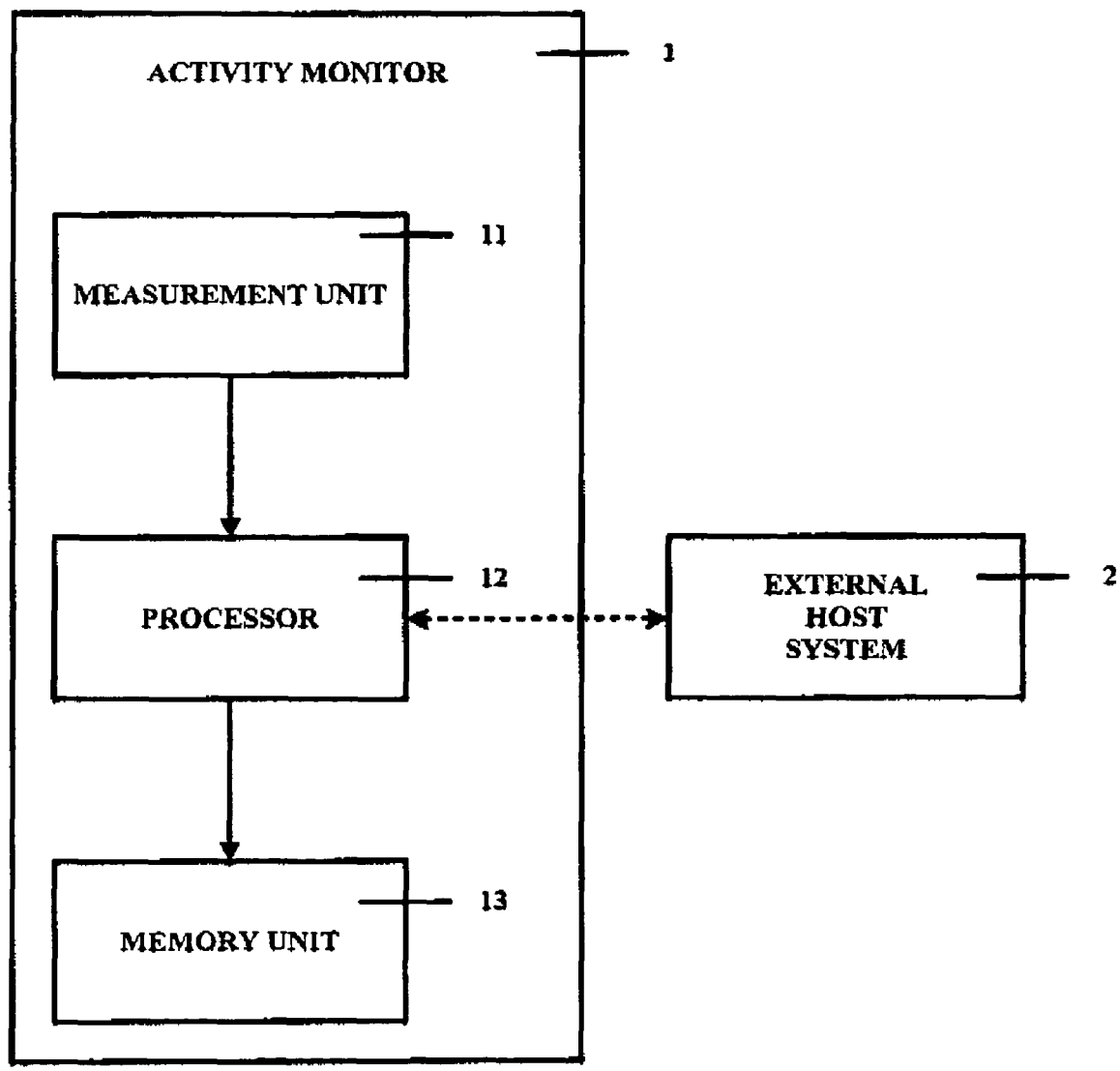

Cliff Randell and Henk Muller, "Context Awareness by Analysing Accelerometer Data", Department of Computer Science, University of Bristol, UK, 2000.*

Cliff Randell and Henk Muller, "An Event-Driven Sensor Architecture for Low Power Wearables", Department of Computer Science, Univesity of Bristol, UK, Jun. 2000.*

* cited by examiner

ACTIVITY MONITORING

The present invention relates to activity monitoring, and in particular, but not exclusively to, activity monitoring of a human being.

The physical activity of a human being is an important determinant of its health. The amount of daily physical activity is considered to be a central factor in the etiology, prevention and treatment of various diseases. Information about personal physical activity can assist the individual in maintaining or improving his or her functional health status and quality of life.

A known system for monitoring human activity is described in the article "A Triaxial Accelerometer and Portable Data Processing Unit for the Assessment of Daily Physical Activity", by Bouten et al., IEEE Transactions on Biomedical Engineering, Vol. 44, NO. 3, March 1997.

According to the known system a triaxial accelerometer composed of three orthogonally mounted uniaxial piezoresistive accelerometers is used to measure accelerations covering the amplitude and frequency ranges of human body acceleration. An individual wears the triaxial accelerometer over a certain period of time. A data processing unit is attached to the triaxial accelerometer and programmed to determine the time integrals of the module of accelerometer output from the three orthogonal measurement directions. These time integrals are summed up and the output is stored in a memory that can be read out by a computer. The output of the triaxial accelerometer bears some relation to energy expenditure due to physical activity and provides as such a measure for the latter.

The known system allows for measurement of human body acceleration in three directions. Using state of the art techniques in the field of integrated circuit technology the accelerometer can be built small and lightweight allowing it to be worn for several days or even longer without imposing a burden to the individual wearing it.

The known systems continuously sample and monitor information from the three accelerometers using three sample analog channels. Since the measurement is carried out continuously, the power consumption of such a device is undesirably high, and so it is desirable to reduce power consumption, which should enable cheaper and/or smaller batteries to be usable.

It is therefore desirable to provide an activity monitor that can overcome these disadvantages.

According to one aspect of the present invention, there is provided an activity monitor comprising a measurement unit including a plurality of motion sensors, operable to produce respective sensor signals indicative of motion experienced thereby and a processor for receiving the sensor signals from the measurement unit and operable to process the signals in accordance with a predetermined method, characterized in that the measurement unit has a single output channel and is operable to output the sensor signals in turn on the output channel.

Figure 2:
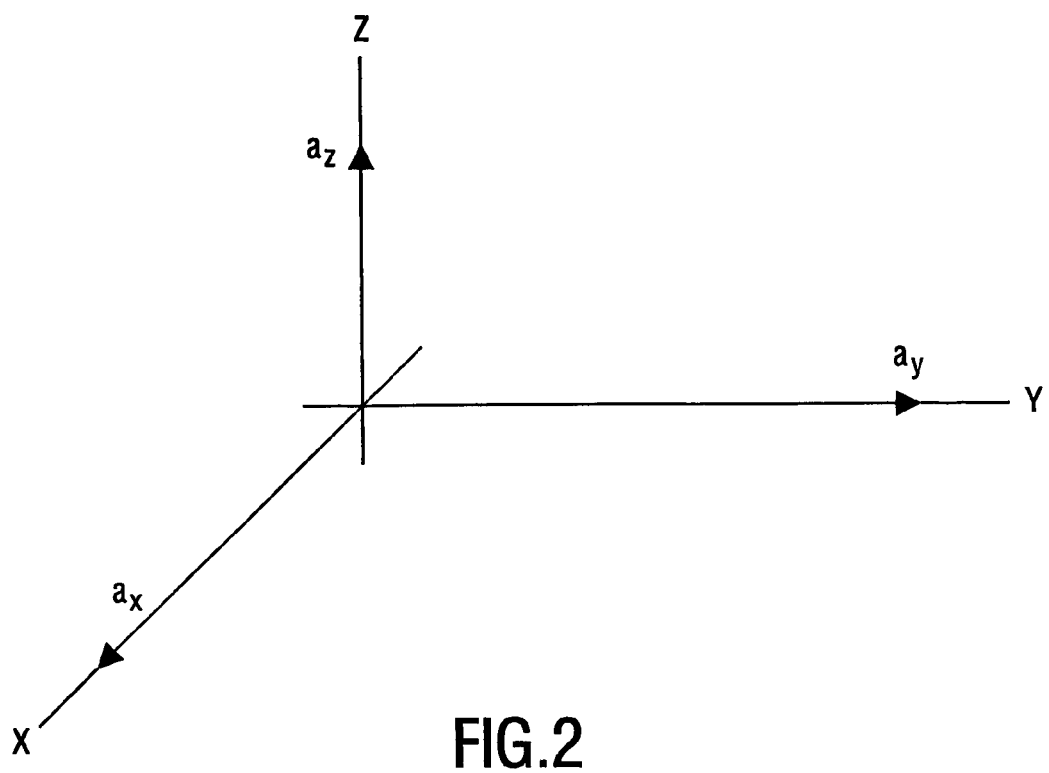
Figure 3:
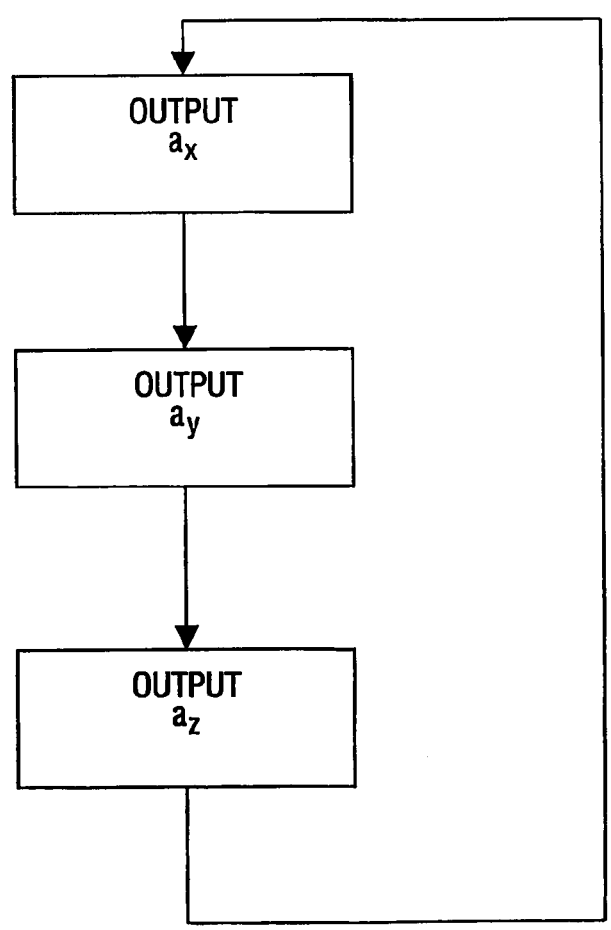
Figure 4:
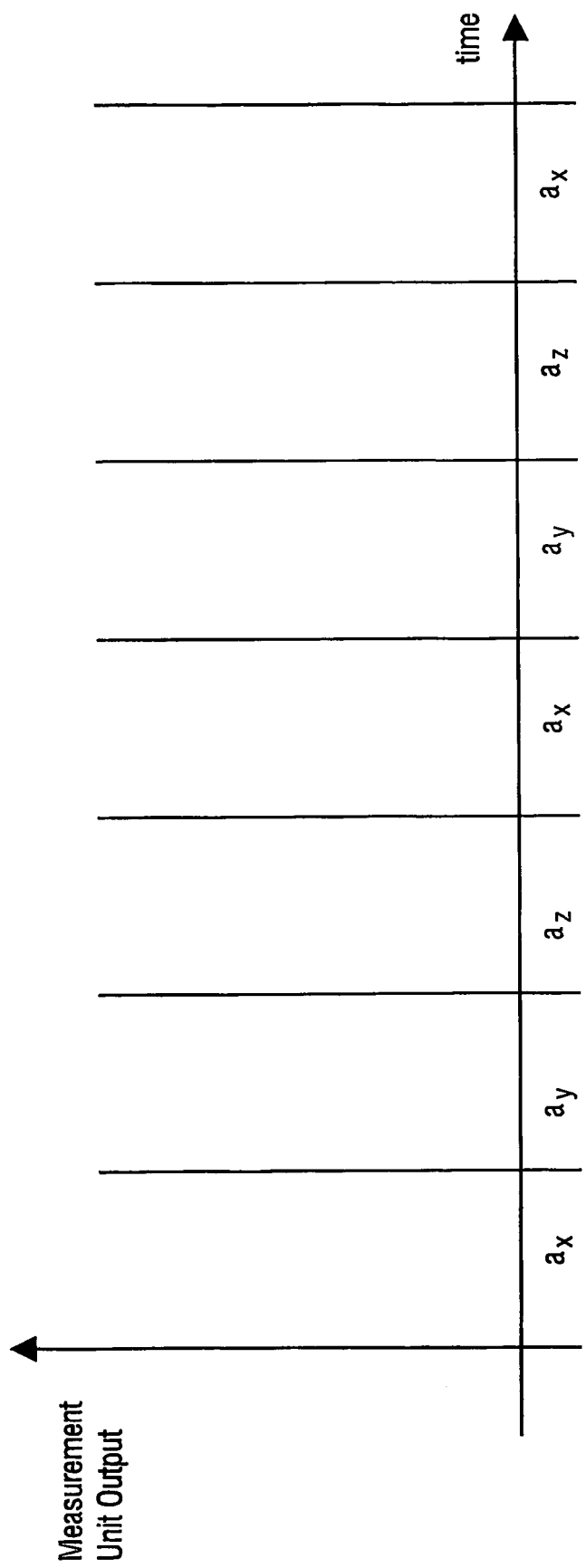

FIG. 1 shows a block diagram schematically showing the components of a system embodying one aspect of the present invention;

FIG. 2 schematically shows the orthogonal outputs of three accelerometers;

FIG. 3 shows a flow diagram of the steps of a method embodying another aspect of the present invention; and FIG. 4 illustrates monitoring of sensor signals in embodiments of the present invention.

FIG. 1 illustrates an activity monitor 1 embodying one aspect of the present invention. The activity monitor 1 comprises a measurement unit 11, a processor 12, and a memory unit 13. The measurement unit 11 is operable to produce data signals indicative of the motion of the activity monitor 1, and to supply those data signals to the processor 12. The processor 12 is operable to process the data signals output from the measurement unit, and is able to store the data signals, or The results of the processing in the memory unit 13. Data can be transferred between the processor and the memory unit 13. The processor 12 is also able to be connected to an external host system 2, which can be a personal computer (PC) or other appropriate systems. The external host system 2 can be used to perform additional processing of the data held in the activity monitor 1.

In use, the activity monitor 1 is attached to the object to be monitored. For purposes of illustration in the following it is assumed that the object is a human individual, although it is clearly possible to apply such an activity monitor for any object. The activity monitor is attached to the individual or object for a certain time period.

The measurement unit comprises three accelerometers which are arranged in mutually orthogonal directions. The accelerometers output data signals which are indicative of the respective accelerations experienced by the accelerometers. The three accelerometers are arranged orthogonal to one another in a conventional manner.

On an individual, these directions are formed "antero-posterior", "medico-lateral" and "vertical", that are denoted as x, y and z, respectively, as shown in FIG. 2. The accelerometers comprise strips of piezo-electric material that is uni-axial and serial bimorph. The strips are fixed at one end thereof.

The piezo-electric accelerometers act as damped mass-spring systems, wherein the piezo-electric strips act as spring and damper. Movements of the strips due to movement of the individual generate an electric charge leading to a measurement of a data signal. In case of human movements the frequency of the data signals lies in the range of 0.1-20 Hz. The amplitude of the data signals lies between −12 g and +12 g. These numbers are discussed in more detail in the article mentioned earlier. Suitable piezo-electric materials to measure such data signals are known to a person skilled in the art.

In accordance with the present invention, the measurement unit has a single output channel, preferably a single analog output channel, which is supplied to the processor 12. The measurement unit operates to output one of the accelerometer signals at any one time via the output channel. The accelerometer signals are output in turn to the output channel via the measurement unit.

In one preferred embodiment of the present invention, the processor is operable to sample the output channel measurement unit in discontinuous fashion. In such a case, the processor samples the output channel from the measurement unit for a predetermined amount of time, and then stops sampling the measurement unit.

In addition to the processor unit operating discontinuously, or as an alternative to that methodology, the measurement unit can operate the output channel discontinuously during the output of each accelerometer signal. FIG. 3 is a flow diagram illustrating the cycled outputs of the measurement unit. As will be appreciated from FIG. 3, each of the outputs $a_x$, $a_y$ and $a_z$, are output in turn from the measurement unit. This is further illustrated in FIG. 4. For the sake of clarity, no particular output signal is shown in FIG. 4, but the time periods during which the respective accelerometer signals are output are shown.

It will be appreciated that reducing the number of channels required from the output of the measurement unit to the processor, can reduce the cost of the activity monitor overall. In addition, varying the sampling rate of the processor means that there are periods of time in which the processor is not active, and so battery power can be conserved during these times. Embodiments of the invention, therefore, can reduce the cost and/or battery power consumption of an activity monitor.

It will be readily appreciated that the accelerometers are merely preferred motion sensors, and that any appropriate motion sensor could be used in an embodiment of the present invention and achieve the advantages of the present invention.

It is emphasized that the term "comprises" or "comprising" is used in this specification to specify the presence of stated features, integers, steps or components, but does not preclude the addition of one or more further features, integers, steps or components, or groups thereof.

The invention claimed is:

1. An activity monitor comprising:
   a measurement unit including a plurality of motion sensors, operable to produce respective sensor signals indicative of motion experienced thereby; and
   a processor connected to the measurement unit by a single output channel, the processor being configured to receive on the single output channel of the measurement unit the sensor signals from the measurement unit and operable to process the signals;
   wherein the measurement unit is configured to operate the single output channel discontinuously in time during output of each motion sensor output signal.

2. The activity monitor as claimed in claim 1, wherein the motion sensors are accelerometers.

3. The activity monitor as claimed in claim 1, wherein the motion sensors are arranged to be mutually orthogonal.

4. The activity monitor as claimed in claim 2 or 3, wherein the processor is operable to sample the single output channel of the measurement unit discontinuously in time.

5. A method of monitoring activity using a plurality of motion sensors which are operable to produce respective sensor signals on a single channel for output to a processor, the sensor signals being indicative of motion experienced thereby, the method comprising the acts of:
   operating the single channel discontinuously in time to produce the respective sensor signals discontinuously in time;
   monitoring the sensor signals provided on the single channel discontinuously in time; and
   processing the sensor signals.

6. The method as claimed in claim 5, further comprising providing the sensor signals on the single channel, wherein the monitoring act monitors in turn the sensor signals on the single channel.

7. The method of claim 5, wherein the processing act samples the single output channel of a measurement unit discontinuously in time, said single output channel including the sensor signals from the plurality of the motion sensors.

8. The method of claim 5, wherein the processing act intermittently samples the single output channel of a measurement unit that outputs the sensor signals.

9. An activity monitor comprising:
   a measurement unit including a plurality of motion sensors, operable to produce respective sensor signals indicative of motion experienced thereby; and
   a processor connected to the measurement unit by a single output channel, the processor being configured to receive the sensor signals from the measurement unit on the single output channel and to process the sensor signals in accordance with a predetermined method,
   wherein the processor is further configured to sample the single output channel of the measurement unit discontinuously in time, and
   wherein the measurement unit is configured to operate the single output channel discontinuously in time during output of each motion sensor output signal.

10. The activity monitor as claimed in claim 9, wherein the motion sensors are accelerometers.

11. The activity monitor as claimed in claim 9, wherein the motion sensors are arranged to be mutually orthogonal.

12. The activity monitor of claim 9, wherein the measurement unit is operable to output the sensor signals in turn on the single output channel.

13. A method of monitoring activity using a plurality of motion sensors which are operable to produce respective sensor signals on a single channel for output to a processor, the sensor signals being indicative of motion experienced thereby, the method comprising the acts of:
   operating the single channel discontinuously in time to produce the respective sensor signals discontinuously in time;
   intermittently monitoring the sensor signals; and
   processing the sensor signals.

14. The method of claim 13, wherein the processing act intermittently samples the single channel of a measurement unit, said single channel including the sensor signals from the plurality of the motion sensors.

15. An activity monitor comprising:
   a measurement unit having a plurality of motion sensors that produce sensor signals indicative of motion; and
   a processor configured to intermittently monitor the sensor signals;
   wherein the measurement unit is connected to the processor by a single output channel, the sensor signals being provided to the processor on the single output channel and the measurement unit being configured to operate the single output channel discontinuously in time.

* * * * *